US008083765B2

(12) United States Patent
Lee et al.

(10) Patent No.: US 8,083,765 B2
(45) Date of Patent: Dec. 27, 2011

(54) SURGICAL INSTRUMENT

(75) Inventors: Woojin Lee, Hopkinton, MA (US);
Andres Chamorro, Natick, MA (US);
Woojoong Lee, The Bottom (NL)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 0 days.

(21) Appl. No.: 12/592,767

(22) Filed: Dec. 2, 2009

(65) Prior Publication Data
US 2010/0168722 A1 Jul. 1, 2010

Related U.S. Application Data

(63) Continuation of application No. 11/649,352, filed on Jan. 2, 2007, now Pat. No. 7,648,519.

(60) Provisional application No. 60/844,130, filed on Sep. 13, 2006.

(51) Int. Cl.
*A61B 17/00* (2006.01)
(52) U.S. Cl. ...................................................... 606/205
(58) Field of Classification Search .......... 606/139–146, 606/205; 403/90, 122
See application file for complete search history.

(56) References Cited

U.S. PATENT DOCUMENTS

| | | | |
|---|---|---|---|
| 2,028,635 A | 1/1936 | Wappler |
| 2,507,710 A | 5/1950 | Grosso |
| 2,790,437 A | 4/1957 | Moore |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,531,855 A | 7/1985 | Wallis |
| 4,688,554 A | 8/1987 | Habib |
| 4,728,020 A | 3/1988 | Green et al. |
| 4,763,669 A | 8/1988 | Jaeger |
| 4,872,456 A | 10/1989 | Hasson |
| 4,880,015 A | 11/1989 | Nierman |
| 4,944,093 A | 7/1990 | Falk |
| 4,944,741 A | 7/1990 | Hasson |
| 4,945,920 A | 8/1990 | Clossick |

(Continued)

FOREIGN PATENT DOCUMENTS

EP 0 095 970 A2 12/1983

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner* — Gary Jackson
*Assistant Examiner* — Eric Blatt
(74) *Attorney, Agent, or Firm* — David M. Driscoll, Esq.

(57) ABSTRACT

A surgical instrument that includes an instrument shaft having proximal and distal ends, a tool disposed from the distal end of the instrument shaft, a control handle disposed from the proximal end of the instrument shaft, a distal motion member for coupling the distal end of the instrument shaft to the tool, a proximal motion member for coupling the proximal end of the instrument shaft to the handle, actuation means extending between the distal and proximal motion members for coupling motion of the proximal motion member to the distal motion member for controlling the positioning of the tool and a locking mechanism for fixing the position of the tool at a selected position and having locked and unlocked states.

26 Claims, 7 Drawing Sheets

U.S. PATENT DOCUMENTS

| | | | |
|---|---|---|---|
| 5,002,543 A | 3/1991 | Bradshaw et al. |
| 5,042,707 A | 8/1991 | Taheri |
| 5,209,747 A | 5/1993 | Knoepfler |
| 5,271,381 A | 12/1993 | Ailinger et al. |
| 5,273,026 A | 12/1993 | Wilk |
| 5,275,608 A | 1/1994 | Forman et al. |
| 5,314,424 A | 5/1994 | Nicholas |
| 5,330,502 A | 7/1994 | Hassler et al. |
| 5,344,428 A | 9/1994 | Griffiths |
| 5,383,880 A | 1/1995 | Hooven |
| 5,386,818 A | 2/1995 | Schneebaum et al. |
| 5,395,367 A | 3/1995 | Wilk |
| 5,405,344 A | 4/1995 | Williamson et al. |
| 5,433,721 A | 7/1995 | Hooven et al. |
| 5,441,494 A | 8/1995 | Ortiz |
| 5,454,827 A | 10/1995 | Aust et al. |
| 5,501,654 A | 3/1996 | Failla et al. |
| 5,508,712 A | 4/1996 | Tom et al. |
| 5,520,678 A | 5/1996 | Heckele et al. |
| 5,599,151 A | 2/1997 | Daum et al. |
| 5,618,294 A | 4/1997 | Aust et al. |
| 5,643,294 A | 7/1997 | Tovey et al. |
| 5,702,408 A | 12/1997 | Wales et al. |
| 5,743,496 A | 4/1998 | Atkinson, Jr. |
| 5,759,151 A | 6/1998 | Sturges |
| 5,766,196 A | 6/1998 | Griffiths |
| 5,772,578 A | 6/1998 | Heimberger et al. |
| 5,823,066 A | 10/1998 | Huitema et al. |
| 5,827,177 A | 10/1998 | Oneda et al. |
| 5,851,208 A | 12/1998 | Trott |
| 5,855,569 A | 1/1999 | Komi |
| 5,873,817 A | 2/1999 | Kokish et al. |
| 5,899,425 A | 5/1999 | Corey Jr. et al. |
| 5,899,914 A | 5/1999 | Zirps et al. |
| 5,904,647 A | 5/1999 | Ouchi |
| 5,916,146 A | 6/1999 | Allotta et al. |
| 5,916,147 A | 6/1999 | Boury |
| 5,921,956 A | 7/1999 | Grinberg et al. |
| 5,928,263 A | 7/1999 | Hoogeboom |
| 5,938,678 A | 8/1999 | Zirps et al. |
| 5,944,713 A | 8/1999 | Schuman |
| 6,126,633 A | 10/2000 | Kaji et al. |
| 6,174,280 B1 | 1/2001 | Oneda et al. |
| 6,210,377 B1 | 4/2001 | Ouchi |
| 6,210,378 B1 | 4/2001 | Ouchi |
| 6,270,453 B1 | 8/2001 | Sakai |
| 6,551,238 B2 | 4/2003 | Staud |
| 6,623,424 B2 | 9/2003 | Hayakawa et al. |
| 6,638,214 B2 | 10/2003 | Akiba |
| 6,656,195 B2 | 12/2003 | Peters et al. |
| 6,666,854 B1 | 12/2003 | Lange |
| 6,752,756 B2 | 6/2004 | Lunsford et al. |
| 6,761,717 B2 | 7/2004 | Bales et al. |
| 7,073,822 B1 | 7/2006 | Renfroe et al. |
| 7,090,637 B2 | 8/2006 | Danitz |
| 7,147,650 B2 | 12/2006 | Lee |
| 2002/0045803 A1 | 4/2002 | Abe et al. |
| 2002/0095175 A1 | 7/2002 | Brock et al. |
| 2002/0133173 A1 | 9/2002 | Brock et al. |
| 2002/0156497 A1 | 10/2002 | Nagase et al. |
| 2002/0177750 A1 | 11/2002 | Pilvisto |
| 2002/0177847 A1 | 11/2002 | Long |
| 2003/0065359 A1 | 4/2003 | Weller et al. |
| 2003/0109898 A1 | 6/2003 | Schwarz et al. |
| 2003/0135204 A1 | 7/2003 | Lee et al. |
| 2003/0149338 A1 | 8/2003 | Francois et al. |
| 2003/0216618 A1 | 11/2003 | Arai |
| 2004/0049205 A1 | 3/2004 | Lee et al. |
| 2004/0111009 A1 | 6/2004 | Adams et al. |
| 2004/0138529 A1 | 7/2004 | Wiltshire et al. |
| 2004/0176751 A1 | 9/2004 | Weitzner et al. |
| 2004/0193146 A1 | 9/2004 | Lee et al. |
| 2004/0236316 A1 | 11/2004 | Danitz et al. |
| 2005/0049580 A1 | 3/2005 | Brock et al. |
| 2005/0107667 A1 | 5/2005 | Danitz et al. |
| 2005/0228440 A1 | 10/2005 | Brock et al. |
| 2005/0251112 A1 | 11/2005 | Danitz et al. |
| 2005/0273084 A1 | 12/2005 | Hinman et al. |
| 2005/0273085 A1 | 12/2005 | Hinman et al. |
| 2006/0195097 A1 | 8/2006 | Evans et al. |
| 2006/0206101 A1 | 9/2006 | Lee |
| 2006/0270909 A1 | 11/2006 | Davis et al. |
| 2007/0250110 A1 | 10/2007 | Lu et al. |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

SURGICAL INSTRUMENT

RELATED APPLICATION

The present application is a continuation of U.S. application Ser. No. 11/649,352 filed on Jan. 2, 2007 now U.S. Pat. No. 7,648,519 which claims priority to commonly owned and U.S. Provisional Patent Application No. 60/844,130 which was filed on Sep. 13, 2006. The content of all of the aforementioned applications are hereby incorporated by reference herein in their entirety.

TECHNICAL FIELD

The present invention relates in general to medical instruments, and more particularly to manually-operated surgical instruments that are intended for use in minimally invasive surgery or other forms of surgical or medical procedures or techniques. The instrument described herein is primarily for a laparoscopic procedure, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the location of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position. Moreover, existing instruments require the use of both hands in order to effectively control the instrument.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical or medical instrument that has a wide variety of applications, through incisions, through natural body orifices or intraluminally.

A further object of the present invention is to provide an improved medical instrument that is characterized by the ability to lock the instrument in a pre-selected particular position.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved medical instrument that can be effectively controlled with a single hand of the user.

SUMMARY OF THE INVENTION

To accomplish the foregoing and other objects, features and advantages of the present invention there is provided a surgical instrument that comprises an instrument shaft having proximal and distal ends; a tool disposed from the distal end of the instrument shaft; a control handle coupled from the proximal end of the instrument shaft; a distal motion member for coupling the distal end of the instrument shaft to the tool; a proximal motion member for coupling the proximal end of the instrument shaft to the handle; actuation means extending between the distal and proximal motion members for coupling motion of the proximal motion member to the distal motion member for controlling the positioning of the tool; and a locking mechanism for fixing the position of the tool at a selected position and having locked and unlocked states with the locking mechanism including a ball and socket arrangement disposed about the proximal motion member and a cinch member for locking the ball and socket arrangement.

In accordance with other aspects of the present invention the surgical instrument may further include a rotation means disposed adjacent the control handle and rotatable relative to the control handle for causing a corresponding rotation of the instrument shaft and tool; at least the proximal motion member may comprise a proximal bendable member, with the rotation means comprising a rotation knob that is adapted to rotate the tool about a distal tool roll axis and being disposed between the control handle and proximal bendable member; the control handle may comprise a pistol grip handle having an engagement horn to assist in holding the handle; the rotation means may comprises a rotation knob that is disposed at the distal end of the handle and the horn is disposed proximally of the rotation knob and on the top of the pistol grip handle; preferably including an actuation lever supported from the pistol grip handle at a pivot point at the proximal end of the handle; the actuation lever may have a free end with a finger loop for receiving a users finger to control the lever; preferably including a tool actuation cable that extends from the tool to the handle, a slider for capturing the proximal end of the tool actuation cable and an actuation lever supported at the handle for controlling the translation of the slider; preferably including a slideway for receiving the slider, a pair of springs disposed in the slider and a rotational barrel disposed between the springs and for holding the proximal end of the tool actuation cable; the ball and socket arrangement may comprise a ball member having a partially spherical portion that mates with a concave socket in the handle; the handle may have a distal collar with the socket formed on the inner surface of the collar and the cinch member may include an annular cinch ring that is disposed about the distal collar; preferably including a tongue and groove interconnection between the cinch ring and collar so as to permit rotation therebetween while preventing axial movement; preferably including a pivot piece on the cinch ring having opposed locked and unlocked positions; and preferably the distal collar has one or more slots to enable the socket to be compressed about the ball member as the cinch ring is locked.

In accordance with another feature of the present invention there is provided a surgical instrument that comprises an instrument shaft having proximal and distal ends; a tool disposed from the distal end of the instrument shaft; a control handle disposed from the proximal end of the instrument shaft; a distal motion member for coupling the distal end of the instrument shaft to the tool; a proximal motion member for coupling the proximal end of the instrument shaft to the handle; actuation means extending between the distal and proximal motion members for coupling motion of the proximal motion member to the distal motion member for controlling the positioning of the tool; said control handle including a pistol grip handle; an actuation lever for controlling the tool and pivotally supported from the handle; and an adjustment member mounted on the lever for adjusting the attitude or angle of the actuation lever relative to a center plane of the handle.

In accordance with still other aspects of the present invention there is provided a surgical instrument wherein the adjustment member includes an adjustment lever for changing the attitude or angle between positive and negative values; wherein the adjustment member includes a beveled washer means; wherein the adjustment lever is supported from the same pivotal support as for the actuation lever; further including an engagement horn to assist in holding the handle and a rotation knob disposed at the distal end of the handle and the horn is disposed proximally of the rotation knob and on the top of the pistol grip handle.

In accordance with still another feature of the present invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members, the control handle having proximal and distal ends, an actuation lever for controlling the distal tool, means for pivotally supporting the actuation lever from the proximal end of the handle at one side thereof, a horn and means for fixedly supporting the horn from the distal end of the handle at an opposite side thereof.

In accordance with other aspects of the present invention there is provided a medical instrument wherein the cable actuation means includes a set of actuation cables that are sufficiently rigid so that each cable is capable of either a pulling or pushing action in controlling the tool; including constraining means for each cable so as to substantially restrain each cable as it extends between the proximal and distal movable members; wherein the control handle includes a pistol grip handle and the actuation lever includes an adjustment member mounted on the lever for adjusting the attitude or angle of the actuation lever relative to a center plane of the handle.

In accordance with a further feature of the present invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members, for controlling the positioning of the distal tool, and means for constraining the cable means along its length so as to enable both a pulling action and a pushing action thereof.

In accordance with further aspects of the present invention there is provided a medical instrument wherein the cable means are constrained along substantially the entire length thereof; and wherein the constraining means includes a shaft filler disposed in the instrument shaft about the cable means.

In accordance with still another feature of the present invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members, for controlling the positioning of the distal tool, and a locking mechanism having locked and unlocked positions, disposed about the proximal movable member and manually controlled so as to fix the position of the proximal movable member relative to the handle in the locked position thereof.

In accordance with other aspects of the present invention there is provided a medical instrument wherein the locking mechanism comprises a ball member and a compressible hub that defines a socket member; wherein the hub is a split hub and the locking mechanism further includes a cinch ring disposed about the split hub and a locking lever mounted on the cinch ring for closing the cinch ring about the hub to lock the hub against the ball member; wherein the cinch ring interlocks with the hub but is able to rotate relative thereto when in the unlocked position; and including a rotation control member adjacent to the proximal movable member for controlling the orientation of the distal movable member and tool.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which.

DETAILED DESCRIPTION OF THE PREFERRED EMBODIMENT

The instrument of the present invention may be used to perform minimally invasive procedures. "Minimally invasive procedure," refers herein to a surgical procedure in which a surgeon operates through a small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen, vessel or cavity, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thoracic, prostate, transvaginal, orthopedic and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

There are a number of unique features embodied in the instrument of the present invention. For example, there is provided a locking mechanism that is constructed using a ball and socket arrangement disposed about the proximal motion member that follows the bending action and in which an annular cinch ring is used to retain the ball and socket arrangement in a fixed particular position, and thus also maintain the proximal and distal bendable members in a particular bent condition, or in other words locked in that position. The cinch ring includes a locking lever that is conveniently located adjacent to the instrument handle and that is easily manipulated to lock and unlock the cinch ring and, in turn, the position of the end effector. The cinch ring is also preferably rotatable to that the locking lever can be positioned conveniently or can be switched (rotated) between left and right handed users. This lock control allows the surgeon one less degree of freedom to concentrate on when performing certain tasks. By locking the bendable sections at a particular position, this enables the surgeon to be more hands-free for controlling other degrees of freedom of the instrument such as manipulation of the rotation knob to, in turn, control the orientation of the end effector.

Another feature of the present invention relates to the manner in which the bending is carried out. In the past, relatively small diameter flexible cables have been used to control bending between the proximal and distal bendable members. However, this has caused a somewhat uneven control in that there was only a "pulling" action by one cable while the opposite cable relaxed. The present invention uses a more rigid cable arrangement so that the bending occurs with both a "pulling" action as well as an opposed "pushing" action. To do this the cables are of larger relative diameter and somewhat rigid, but still have to have sufficient flexibility so that they can readily bend. Also, the cables are constrained along their length so as to prevent cable deflection or buckling, particularly during the "pushing" phase of a cable.

Still another feature is the pistol grip arrangement and the control lever which has an end gimbal construction that provides for a more precise control of the actuation lever and the corresponding actuation of the end effector. Also the control lever in accordance with the present invention is provided with a means to control the attitude of the control lever to compensate for different configurations of hands, particularly to compensate for the different length fingers of a user.

Figures 1, 2:
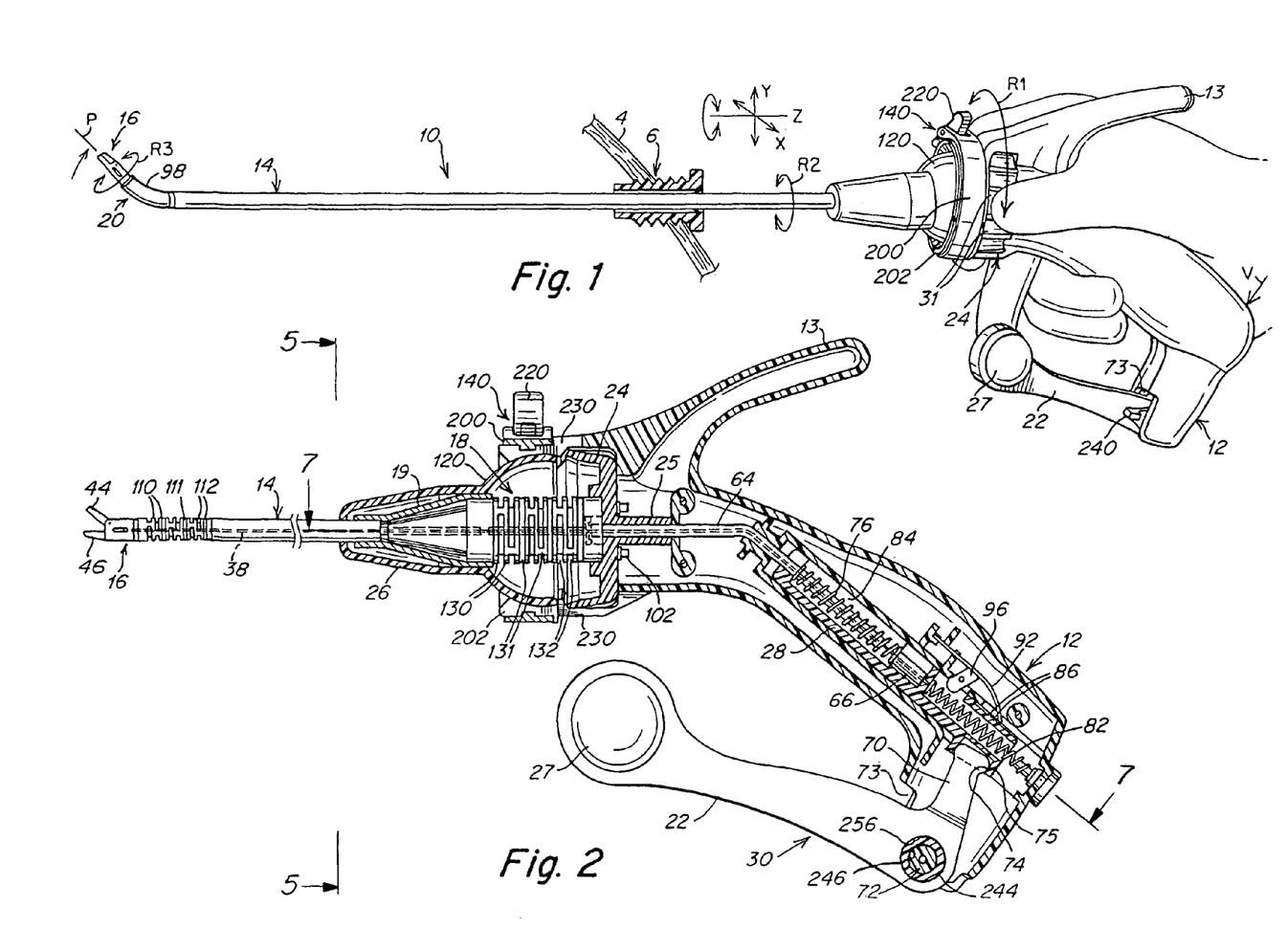
FIG. 1 is a perspective view of a preferred embodiment of the instrument of the present invention illustrating the instrument being grasped by a user and further schematically illustrating the instrument disposed at an operative site.
FIG. 2 is a cross-sectional side view of the instrument of FIG. 1 by itself and with the cross-sectional view primarily illustrating the proximal or handle end of the instrument.

FIG. 1 is a perspective view of one embodiment of the surgical instrument 10 of the present invention. In this surgical instrument both the tool and handle motion members or bendable members are capable of bending in any direction. They are interconnected via cables (preferably four cables) in such a way that a bending action at the proximal member provides a related bending at the distal member. The proximal bending is controlled by a motion or deflection of the control handle by a user of the instrument. In other words the surgeon grasps the handle and once the instrument is in position any motion (deflection) at the handle immediately controls the proximal bendable member which, in turn, via cabling controls a corresponding bending or deflection at the distal bendable member. This action, in turn, controls the positioning of the distal tool.

The proximal member is preferably generally larger than the distal member so as to provide enhanced ergonomic control. In the illustrated embodiment the ratio of proximal to distal bendable member diameters may be on the order of three to one. In one version in accordance with the invention there may be provided a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

As has been noted the, amount of bending motion produced at the distal bending member is determined by the dimension of the proximal bendable member in comparison to that of the distal bendable member. In the embodiment described the proximal bendable member is generally larger than the distal bendable member, and as a result, the magnitude of the motion produced at the distal bendable member is greater than the magnitude of the motion at the proximal bendable member. The proximal bendable member can be bent in any direction (about 360 degrees) controlling the distal bendable member to bend in either the same or an opposite direction, but in the same plane at the same time. Also, as depicted in FIG. 1, the surgeon is able to bend and roll the instrument's tool about its longitudinal axis T to any orientation simply by rolling the axial rotation knob about rotation direction R1.

In this description reference is made to bendable members. These members may also be referred to as turnable members, bendable sections or flexible members. In the descriptions set out herein, terms such as "bendable section," "bendable segment," "bendable member," or "turnable member" refer to an element of the instrument that is controllably bendable in comparison to an element that is pivoted at a joint. The term "movable member" is considered as generic to bendable sections and joints. The bendable elements of the present invention enable the fabrication of an instrument that can bend in any direction without any singularity and that is further characterized by a ready capability to bend in any direction, all preferably with a single unitary or uni-body structure. A definition of a "unitary" or "uni-body" structure is—a structure that is constructed only of a single integral member and not one that is formed of multiple assembled or mated components—.

A definition of these bendable members is—an instrument element, formed either as a controlling means or a controlled means, and that is capable of being constrained by tension or compression forces to deviate from a straight line to a curved configuration without any sharp breaks or angularity—. Bendable members may be in the form of unitary structures, such as shown herein in FIGS. 1 and 2, may be constructed of engageable discs, or the like, may include bellows arrangements or may comprise a movable ring assembly. For other forms of bendable members refer to co-pending application Ser. No. 11/505,003 filed on Aug. 16, 2006 and Ser. No. 11/523,103 filed on Sep. 19, 2006, both of which are hereby incorporated by reference herein in their entirety.

FIG. 1 shows a preferred embodiment of the instrument of the present invention. Further details are illustrated in FIGS. 2 through 15. FIG. 1 depicts the surgical instrument 10 in position, as may occur during a surgical procedure. For example, the instrument may be used for laparoscopic surgery through the abdominal wall, such as shown at 4 in FIG. 1. For this purpose there is provided an insertion site at which there is disposed a cannula or trocar 6. The shaft 14 of the instrument 10 is adapted to pass through the cannula or trocar 6 so as to dispose the distal end of the instrument at the operative site. The end effector 16 is depicted in FIG. 1 at such an operative site with the cannula or trocar 6 at the incision point in the skin 4. The embodiment of the instrument shown in FIG. 1 is typically used with a sheath 98 to keep bodily fluids from entering the distal bending member 20.

A rolling motion can be carried out with the instrument of the present invention. This can occur by virtue of the rotation of the rotation knob 24 relative to the handle 12 about axis T (refer to FIG. 3). This is represented in FIG. 1 by the rotation arrow R1. When the rotation knob 24 is rotated, in either direction, this causes a corresponding rotation of the instrument shaft 14. This is depicted in FIG. 1 by the rotational arrow R2. This same motion also causes a rotation of the distal bendable member and end effector 16 about an axis that corresponds to the instrument tip, depicted in FIGS. 1 and 3 as about the longitudinal tip or tool axis P.

Any rotation of the rotation knob 24 while the instrument is locked (or unlocked) maintains the instrument tip at the same angular position, but rotates the orientation of the tip (tool). For a further explanation of the tip rotational feature refer to co-pending application Ser. No. 11/302,654, filed on Dec. 14, 2005, particularly FIGS. 25-28, which is hereby incorporated by reference in its entirety.

Figures 3, 4A, 4B, 4C, 4D:
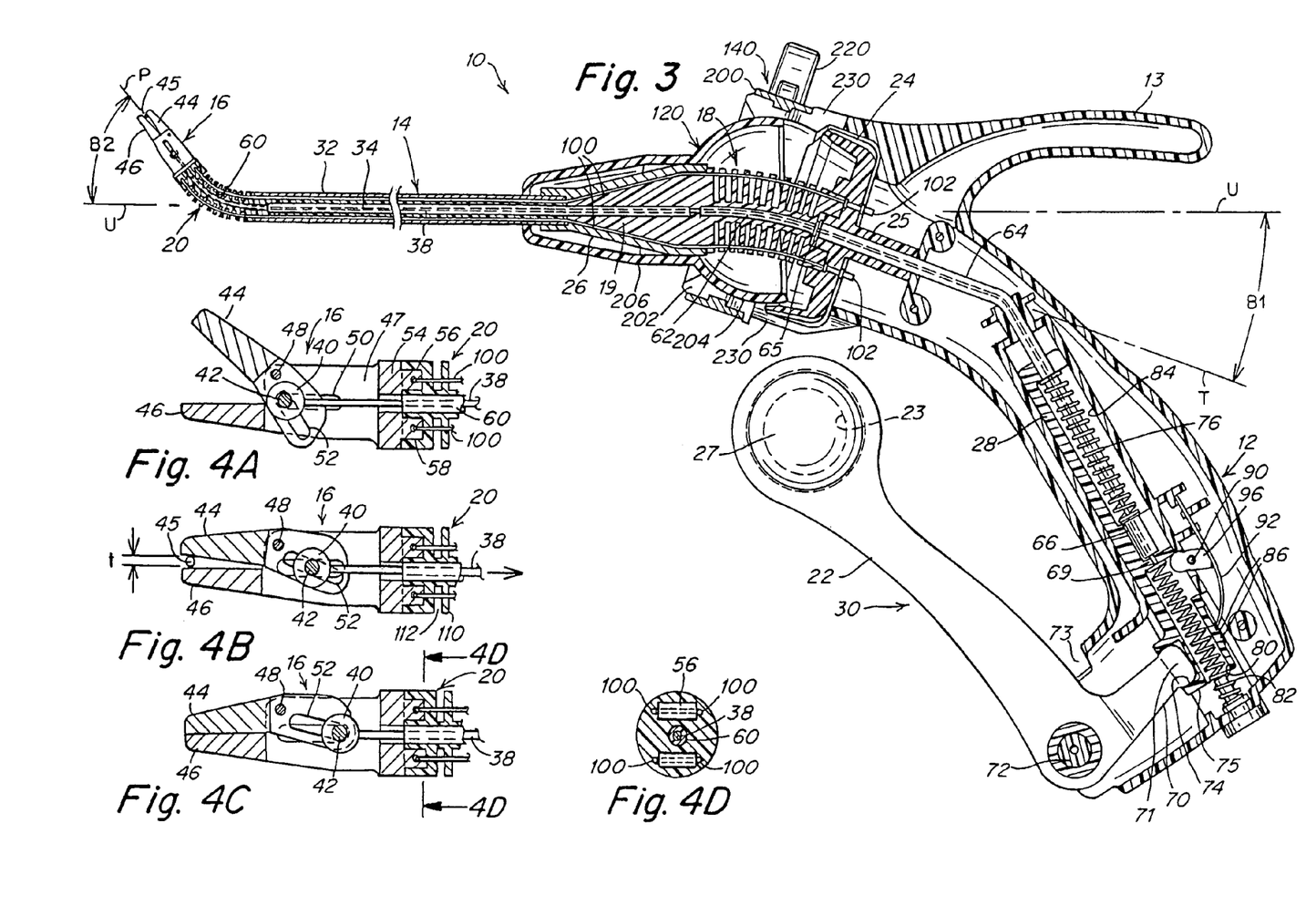
FIG. 3 is an enlarged cross-sectional side view showing the instrument of FIG. 2 in an angled relationship and with the jaws closed on a needle.
FIGS. 4A-4C are illustrative cross-sectional side views at the distal end of the medical instrument, and with the movable jaw in different respective positions.
FIG. 4D is a radial cross-sectional view taken along line 4D-4D of FIG. 4C.

The handle 12, via proximal bendable member 18, may be tilted at an angle to the instrument shaft longitudinal center axis. This tilting, deflecting or bending may be considered as in the plane of the paper. By means of the cabling this action causes a corresponding bend at the distal bendable member 20 to a position wherein the tip is directed along an axis and at a corresponding angle to the instrument shaft longitudinal center axis. The bending at the proximal bendable member 18 is controlled by the surgeon from the handle 12 by manipulating the handle in essentially any direction including in and out of the plane of the paper in FIG. 1. This manipulation directly controls the bending at the proximal bendable member. Refer to FIG. 3 in which there is shown the axis U corresponding to the instrument shaft longitudinal axis. Refer also to the proximal bend angle B1 between axes T and U, and the corresponding distal bend angle B2 between axes U and P.

Thus, the control at the handle is used to bend the instrument at the proximal motion member to, in turn, control the positioning of the distal motion member and tool. The "position" of the tool is determined primarily by this bending or motion action and may be considered as the coordinate location at the distal end of the distal motion member. Actually, one may consider a coordinate axis at both the proximal and distal motion members as well as at the instrument tip. This positioning is in three dimensions. Of course, the instrument positioning is also controlled to a certain degree by the ability of the surgeon to pivot the instrument at the incision point (cannula 6). The "orientation" of the tool, on the other hand, relates to the rotational positioning of the tool, from the proximal rotation control member, about the illustrated distal tip or tool axis P. In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

The surgical instrument of FIG. 1 shows a preferred embodiment of a surgical instrument 10 according to the invention in use and may be inserted through a cannula at an insertion site through a patient's skin. Many of the components shown herein, such as the instrument shaft 14, end effector 16, distal bending member 20, and proximal bending member 18 may be similar to and interact in the same manner as the instrument components described in the co-pending U.S. application Ser. No. 11/185,911 filed on Jul. 20, 2005 and hereby incorporated by reference herein in its entirety. Many other components shown herein, particularly at the handle end of the instrument may be similar to components described in the co-pending U.S. application Ser. No. 11/528,134 filed on Sep. 27, 2006 and hereby incorporated by reference herein in its entirety. Also incorporated by reference in their entirety are U.S. application Ser. No. 10/822,081 filed on Apr. 12, 2004; U.S. application Ser. No. 11/242,642 filed on Oct. 3, 2005 and U.S. application Ser. No. 11/302,654 filed on Dec. 14, 2005, all commonly owned by the present assignee.

Figure 5:
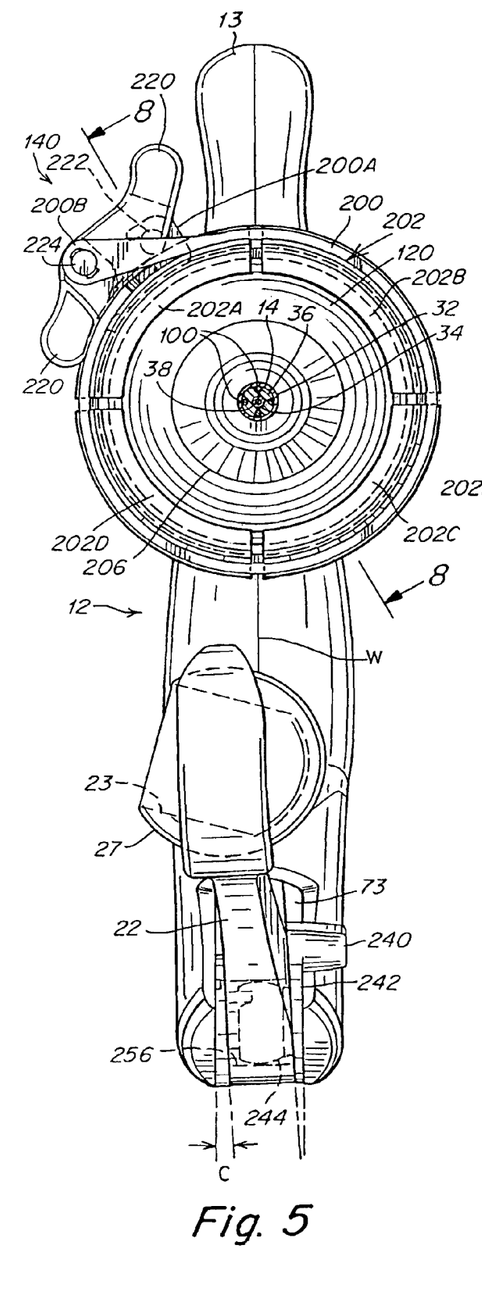
FIG. 5 is a cross-sectional front view of the instrument of FIG. 1 as taken along line 5-5 of FIG. 2 and showing the locking lever in its locked position.
Figure 6:
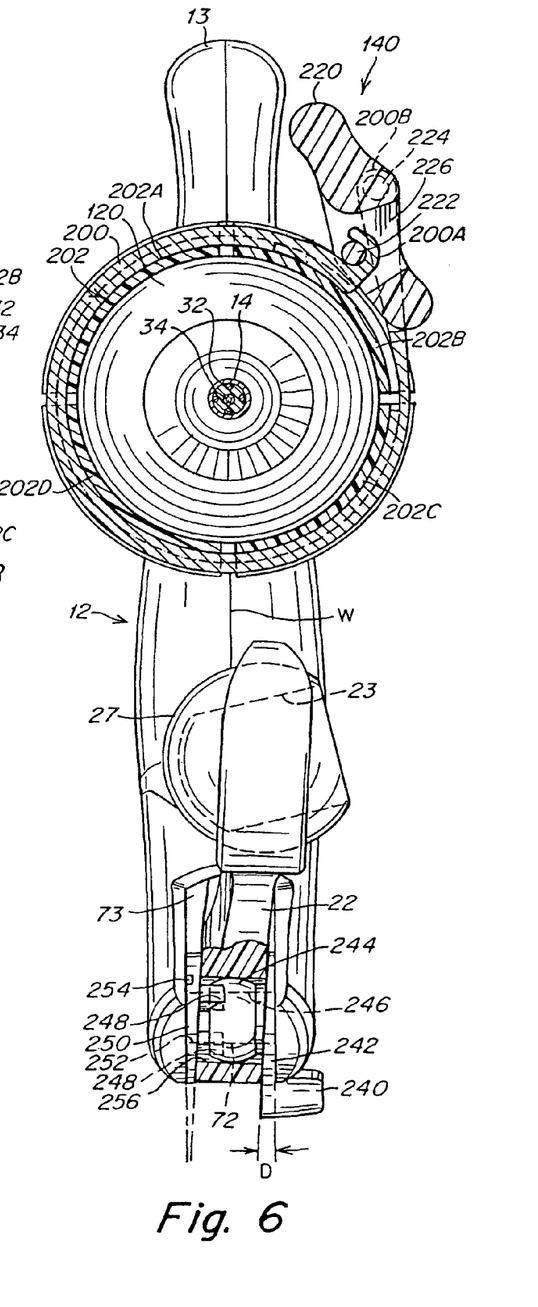
FIG. 6 is a cross-sectional front view of the instrument illustrated in FIG. 5 showing the locking lever in its unlocked position, and further illustrating some components of the instrument broken away to illustrate certain adjustments that can be made to accommodate the user of the instrument.
Figure 7:
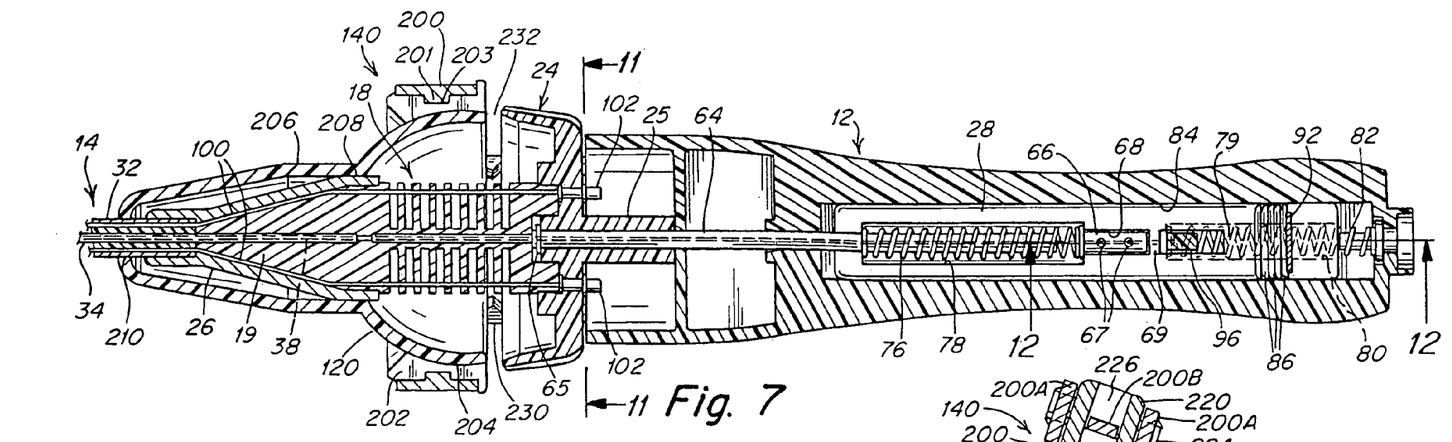
FIG. 7 is a cross-sectional plan view taken along line 7-7 of FIG. 2.
Figures 8, 10:
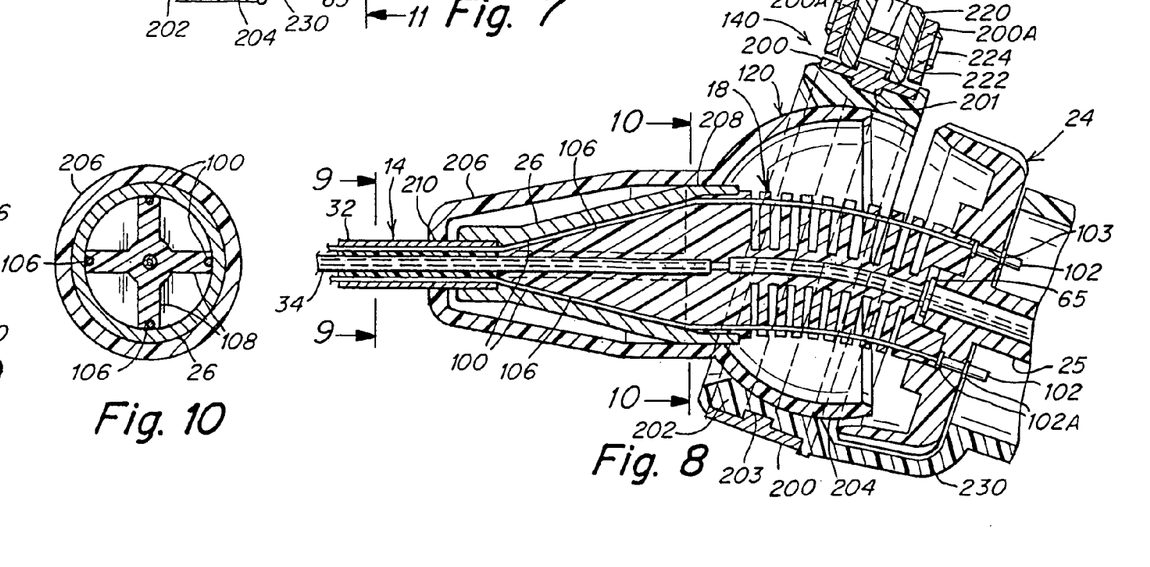
FIG. 8 is a fragmentary cross-sectional view taken along line 8-8 of FIG. 5 but showing the instrument in an angled relationship.
FIG. 10 is a cross-sectional view at the adapter of the instrument as taken along line 10-10 of FIG. 8.

As illustrated in FIGS. 3-8, the control between the proximal bendable member 18 and distal bendable member 20 is provided by means of the bend control cables 100. In the illustrated embodiment four such control cables 100 are provided in order to provide the desired all direction bending. However, in other embodiments of the present invention fewer or less numbers of bend control cables may be used. The bend control cables 100 extend through the instrument shaft 14 and through the proximal and distal bendable members such as shown in FIGS. 3 and 4. The bend control cables 100 are constrained along substantially their entire length so as to facilitate both "pushing" and "pulling" action in accordance with one aspect of the present invention as discussed in further detail hereinafter. The cables 100 are also constrained as they pass over the conical cable guide portion 19 of the proximal bendable member, and through the proximal bendable member. Refer, for example, to FIGS. 7 and 8.

The locking means of the present invention interacts with the novel ball and socket arrangement to lock and unlock the positioning of the cables which in turn control the angle of the proximal bending member and thus the angle of the distal bendable member and end effector. This lock control allows the surgeon one less degree of freedom to concentrate on when performing certain tasks. By locking the bendable sections at a particular position, this enables the surgeon to be more hands-free for controlling other degrees of freedom of the instrument such as manipulation of the rotation knob 24 and, in turn, orientation of the end effector.

The instrument shown in FIG. 1 is of a pistol grip type. However, the principles of the present invention may also apply to other forms of handles such as a straight in-line handle. In FIG. 3 there is shown a jaw clamping means 30 that is comprised mainly of the lever 22 which has a single finger hole for controlling the lever and also includes a related release function controlled directly by the lever 22 rather than a separate release button. The release function is used to release the actuated or closed tool, and is discussed in further detail hereinafter.

In the instrument that is illustrated the handle end of the instrument may be tipped in any direction as the proximal bendable member is constructed and arranged to enable full 360 degree bending. This movement of the handle relative to the instrument shaft bends the instrument at the proximal bendable member 18. This action, in turn, via the bend control cables 100, bends the distal bendable member in the same direction. As mentioned before, opposite direction bending can be used by rotating or twisting the control cables through 180 degrees from one end to the other end thereof. Refer to the schematic perspective view of FIG. 15 for an illustration of the straight cabling used in the illustrated instrument.

In the embodiment described herein, the handle 12 is in the form of a pistol grip and includes a horn 13 to facilitate a comfortable interface between the action of the surgeon's hand and the instrument. The tool actuation lever 22 is shown in FIGS. 1-3 pivotally attached at the base of the handle. The lever 22 actuates a slider 28 that controls a tool actuation cable 38 that extends from the slider to the distal end of the instrument. The cable 38 controls the opening and closing of the jaws, and different positions of the lever control the force applied at the jaws.

Figure 11:
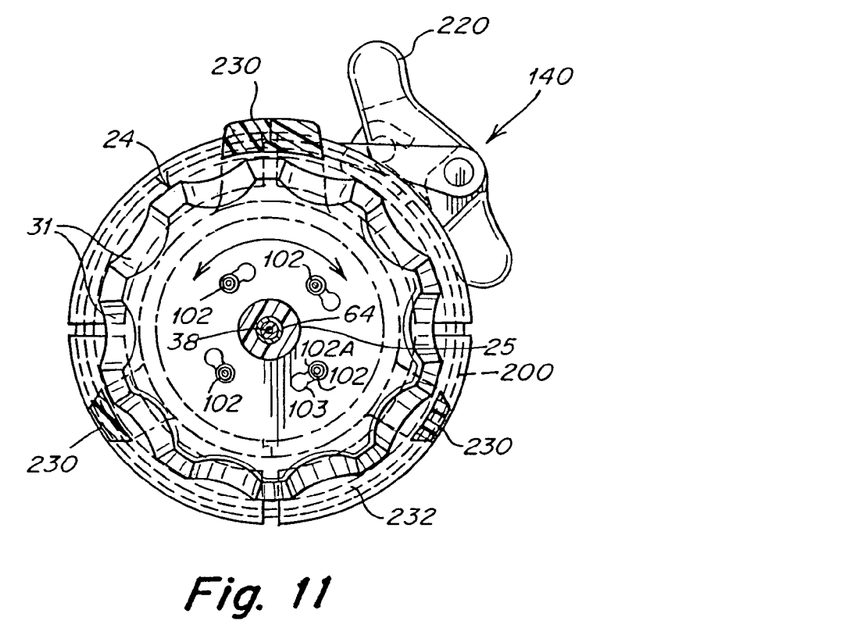
FIG. 11 is a cross-sectional view at the rotation knob of the instrument as taken along line 11-11 of FIG. 7.

The shape of the handle allows for a comfortable and substantially one-handed operation of the instrument as shown in FIG. 1. As shown in FIG. 1, the surgeon may grip the handle 12 between his palm and middle finger with the horn 13 nestled in the crook between his thumb and forefinger. This frees up and positions the forefinger and thumb to rotate the rotation knob 24 using the finger indentions 31 that are disposed on the peripheral surface of the rotation knob, as depicted in FIG. 11. In both locked and unlocked positions of the instrument the rotation knob is capable of controlled rotation to control axial rotation at the tip of the instrument about the distal tool tip axis P, as represented by the rotation arrow R3 in FIG. 1.

In the disclosed embodiment there is provided at the tool closing lever 22 a fingertip engaging recess 23 in a gimbaled ball 27. The free end of the lever 22 supports the gimbaled ball 27 which has a through hole or recess 23 which receives one of the fingers of the user. The ball 27 is free to at least partially rotate in three dimensions in the lever end. The surgeon may grip the handle between the palm, ring and pinky fingers with the horn 13 nestled in the crook between his thumb and forefinger and operate the rotation knob 24 as previously described. The surgeon may then operate the jaw clamping lever 22 with the forefinger or middle finger.

The gimbal is in the form of a ball in a socket, in which the ball 27 is free to be rotated in the socket, and in which the socket is defined in the lever free end. In this embodiment, rather than having the hole or recess 23 go completely through the ball there is preferably provided a blind hole in the ball. This blind hole is shown in FIGS. 5 and 6. The ball is free to rotate in the lever end and thus the ball can also be rotated to alternate positions corresponding to either a right-handed (FIG. 5) or left-handed (FIG. 6) user. The blind hole (in comparison to a through hole) enables the user to have a firmer grip of the lever and thus enhanced control of the lever action.

Reference is now made to FIGS. 2-4. In this instrument the distal bendable member 20 is shown without any protective sheath so as to show some of the details of the distal bendable member 20. The distal bendable member is comprised of spaced discs 110 that define therebetween spaced slots 112. Ribs 111 may connect between adjacent discs in a manner similar to that described in the afore-mentioned U.S. application Ser. No. 11/185,911.

Refer also now to FIGS. 4A-4D for further details of the tool end of the instrument. FIG. 4A depicts the jaws in a fully open position. FIG. 4B depicts the jaws grasping a needle. FIG. 4C depicts the jaws fully closed. FIG. 4D is a cross-sectional view taken along line 4D-4D of FIG. 4C. The end effector 16 is comprised of a pair of jaws 44 and 46. The jaws 44 and 46 may be used to grasp a needle 45 or other item as shown in FIG. 3. The upper jaw 44 fits within a channel 47 in the lower jaw 46. A pivot pin 48 is used between the jaws to enable rotation therebetween. A translation pin 42 extends through the slot 50 of jaw 46 and the slot 52 of jaw 44 and engages with the hole in the distal cable end connector 40. The connector 40 is secured to the very distal end of the jaw actuator cable 38 and is positioned within a channel of the jaw 44. When the lever 22 is in its rest position, as depicted in FIG. 2, the jaws are fully open. In that position the pin 42 is at a more distal location maintaining the jaws in an open position. As the cable 38 is pulled, such as proximally in FIG. 3, then the pin 42 moves to the right in the slots 50 and 52 causing the jaws 44 and 46 to pivot toward a closed position.

Figure 15:
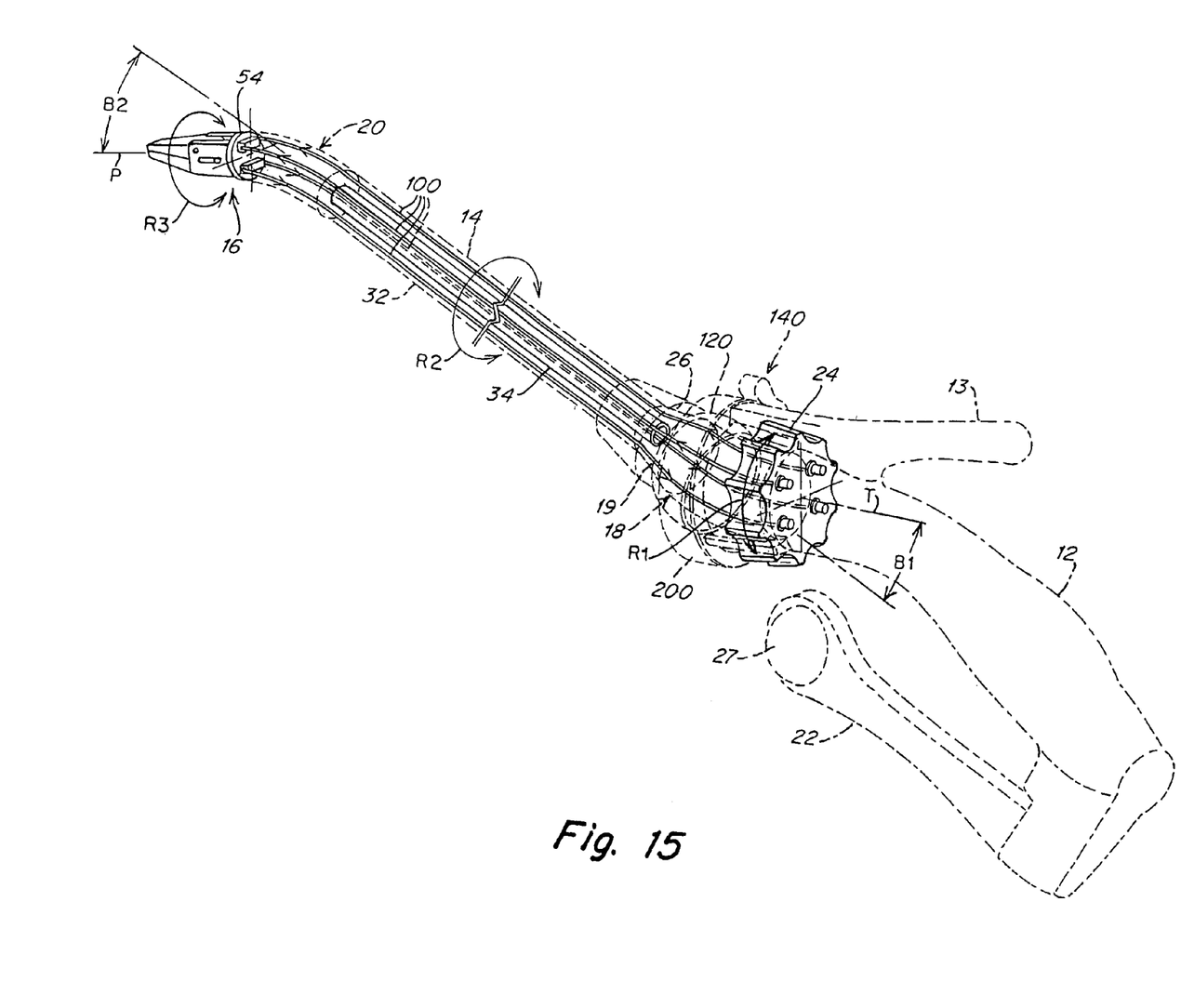
FIG. 15 is a schematic perspective view of the instrument illustrated herein.

FIGS. 4A-4D also depicts an end wall or plate 54 of the jaw 46. One end of the distal bendable member 20 is urged against this end wall 54. The member 20 may be secured to the wall 54 by an appropriate means. In one embodiment, the cabling tension itself of the instrument holds the members together. On the end wall 54 there are disposed a pair of anchors 56 and 58 for the flex control cables 100. FIG. 4D illustrates four such cables 100. The distal end of the distal bendable member 20 may be provided with pockets for receiving the anchors 56 and 58. The anchors 56 and 58 are firmly attached to the end wall 54. Refer also to FIG. 15 for an illustration of the cabling and the connections thereof at opposite ends of each cable 100.

The rotation knob 24 is provided with a proximal hub 25 which supports the proximal end of the proximal bending member 18. During assembly, the cables 100 which protrude from the proximal end of the proximal bending member 18, after the assembly of the end effector 16, inner and outer shafts 32, 34, adapter 26 and proximal bending member 18, are passed through the four terminal wire crimps or lugs 102 which are keyed into passages in the hub 25. The cables are tensioned and crimped and excess cable material is trimmed off. This arrangement holds all the elements together between the end effector 16 and the rotation knob hub 25 and, in turn, the rotation knob 24.

As indicated previously, the rotation knob 24 is formed with a hub 25 on its proximal side that is supported on the center wire conduit 64 which extends from the rotation knob 24 back to the slider 28. An e-ring 65 retains the hub 25 in a rotational relationship relative to the conduit 64. The conduit 64 is supported in a fixed position by internal means of the handle 12. The knob 24 is readily accessible through a gap 232 between the split hub 202 and the distal end of the handle. See the gap 232 in FIG. 7. The rotation knob 24 has four keyhole shaped slots 103 (FIG. 11) that mate with terminal wire crimps 102A-102D that enables a "push-pull" effect on the cables 100 when the handle is bent in relation to the shaft in contrast to past versions where the cables were in a spring-loaded "pull" relationship relative to the rotation knob. Because of this "push-pull" action, biasing springs associated with each cable are not used.

As indicated previously, the end effector or tool 16 is actuated by means of a jaw actuation mechanism or jaw clamping means 30 which is comprised primarily of the elongated lever 22. The lever 22 is supported from the housing at the lever pivot pin 72. Refer to FIGS. 2 and 3. The closing of the lever 22 against the handle 12 acts upon the slider 28 which is used to capture the very proximal end of the actuation cable 38. When the slider 28 is in the position depicted in FIG. 2, it is noted that the end effector jaws are fully open. In that position the slider 28 is disposed at the more distal end of the slideway 84. The slideway 84 is part of the internal support in the handle 12. When the slider 28 is moved proximally, as depicted in FIG. 3, then the jaws are moved toward a closed position grasping the needle 45.

The instrument shaft 14 includes an outer shaft tube 32 that may be constructed of a light weight metal material or may be a plastic material. See the cross-sectional view of FIG. 9 taken through the instrument shaft. The proximal end of the tube 32 is received by the adaptor 26, as depicted in FIGS. 7 and 8. The distal end of the tube 32 is secured to the distal bendable member 20. Within the outer shaft tube 32 there is provided a support tube 34 that is preferably constructed of a plastic material. Tube 34 extends between the distal bendable or flexible member 20 and the proximal bendable or flexible member 18. The jaw actuator cable 38 extends within this support tube 34.

One of the features of the present invention is the cable scheme that uses bend control cables that are relatively stiff and yet are bendable. The stiffer cables allow for, not only "pulling", but also "pushing" action thereof. This enables enhanced control via the cabling as control is provided, not only when a cable is "pulled", but also when a cable is "pushed". This makes for a more uniform control via the cables. To enable, not only a "pulling" action, but also a "pushing" action, the cables 100 are supported in relatively narrow lumens or passageways to prevent buckling when being pushed. This is facilitated by, inter alia, the provision of a shaft filler 36. To allow for the "pushing" action in particular the cables are confined so that they do not distort within the instrument itself.

Figure 9:
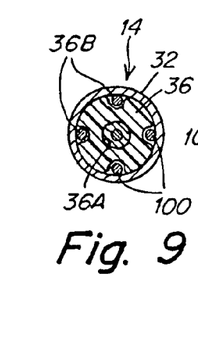
FIG. 9 is an enlarged cross-sectional view at the instrument shaft taken along line 9-9 of FIG. 8.

The shaft filler 36 is disposed between the tubes 32 and 34 and is used to hold the cables in place within the instrument shaft itself. As can be seen in FIG. 9, the shaft filler has a central lumen 36A for the inner shaft support tube 34 and four lengthwise grooves 36B that accommodate and allow a snug sliding fit for the cables 100. The conical portion 19 of the proximal bending member 18 has four cable guide grooves 106 disposed at 90 degree intervals about its outer surface that capture each cable in a sliding relationship with the adapter 26. Each of the guide grooves is formed in a separate diametrically disposed wing 108 of the conical portion 19. The adaptor 26 may also be provided with accommodating grooves for the cables 100. Refer also to the cross-sectional view of FIG. 10 for an illustration of the cable guide and constraining arrangement. Thus, the cables are constrained along their length in grooves or passages. Each of the cables is preferably unsupported for only a short distance such as the distance of the slots 132 shown in FIGS. 2 and 3, or like slots at the distal bendable member.

The jaw actuator cable 38 terminates at its respective ends at the end effector (connector 40) and the rotation barrel 66 (see FIG. 3). Within each of the bendable sections or bendable members 18 and 20 there is provided a plastic tube. This includes a distal tube 60 and a proximal tube 62. Both of these tubes may be constructed of a plastic such as polyethyletherkeytone (PEEK). The material of the tubes is sufficiently rigid to retain the cable 38 and yet is flexible enough so that it can readily bend with the bending of the bendable members 18 and 20. The tubes have a sufficient strength to receive and guide the cable, yet are flexible enough so that they will not kink or distort, and thus keep the cable in a proper state for activation, and also defines a fixed length for the cable. The tubes are longitudinally stiff, but laterally flexible.

The proximal bendable member 18, like the distal bendable member 20, may also be constructed as a unitary or uni-body slotted structure including a series of flexible discs 130 that define therebetween slots 132, as shown in FIG. 2. A "unitary" or "uni-body" structure may be defined as one that is constructed for use in a single piece and does not require assembly of parts. Connecting ribs 131 are illustrated as extending between adjacent discs 130. Both of the bendable members preferably have a rib pattern in which the ribs are disposed at a preferred 60 degree variance from one rib to an adjacent rib. This has been found to provide an improved bending action. It was found that by having the ribs disposed at intervals of less than 90 degrees therebetween improved bending was possible. The ribs may be disposed at intervals of from about 35 degrees to about 75 degrees from one rib to an adjacent one. By using an interval of less than 90 degrees the ribs are more evenly distributed. As a result the bending motion is more uniform at any orientation. In the present invention both of the bendable members may be made of a highly elastic polymer such as PEBAX (Polyether Block Amide), but could also be made from other elastic and resilient materials.

The lever 22 in FIG. 2 is shown in the lowermost position which may be considered as the "at rest" position. This is also substantially the same position illustrated in FIGS. 7 and 12. This would be achieved by either action of the return spring 82 in the bore 80 of the slider 28 in certain instruments or by the surgeon manually moving the lever to that position in other embodiments of the instrument where a return spring is not used.

FIGS. 2 and 3 illustrate the lever 22 passing through a slot 73 in the handle and being mounted to a pivot pin 72. An arm 70 of the lever 22 has a cylindrical head 71 which mates with a recess 74 in a boss 75 at the proximal end of the slider 28. The slider 28 sits in the slideway 84 and moves proximally and distally in response to the lever position and/or return spring action. The slider 28 carries the rotatable barrel 66 clamped to the push/pull cable 38 by means of the set screws 67 or the like. The barrel 66 is rotatable in response to the rotation of the instrument shaft and end effector. Refer also to FIG. 7 for further details of the slider mechanism. The barrel 66 sits in a slot 68 which is open to a contiguous slot 78 at one end and is closed by a wall 69 at its other end. The wall 69 has a through hole which acts as a guide for the push/pull cable 38 that protrudes from the proximal end of the barrel 66, and thus guides the barrel action itself. The barrel 66 is urged against the wall by a compression spring 76 that is disposed in the slot 78. The position of the lever, as depicted in FIG. 2 has the jaws fully open as also shown in FIG. 4A. Refer to co-pending Ser.

No. 11/528,134 filed on Sep. 27, 2006 for further details of the operation of the lever and slider.

The jaw clamping lever 22 is also adjustable for left and right handed operation as well as a range of adjustment from angle C in FIG. 5 to angle D in FIG. 6. This is accomplished by means of a cam lever 240 at the base of the handle that rotates approx. 180 degrees about shaft 72 that also supports jaw clamping lever 22. The control by the lever 240 may also be by rotation through other angles. The cam lever 240 basically adjusts the attitude of the clamping lever 22 relative to a center line or center plane of the handle as represented by the line or plane W in FIGS. 5 and 6 which illustrate the opposite direction attitudes depending on the position of the lever 240. This adjustment can be made based on whether the user is right handed or left handed, or can be made on the basis of some other characteristic of the hand of the user such as finger length.

The cam lever 240 includes a wedge shaped washer 242 with a truncated ball 244 formed on the inside sloped surface of the washer portion. The ball and washer have a through hole 246 that fits over shaft 72 and allows the lever to pivot about the shaft 72 upwardly or downwardly from a front to rear position relative to the base of the handle as seen in FIGS. 5 and 6. The ball 244 has mating features shown at 248 in FIG. 6 and preferably in the form of two slots that mate with two lugs on a cam disk 250. These mating features synchronize rotation of the lever 240 and cam disk 250. Cam disk 250 is also basically a wedge shaped washer with a through hole 252 that allows it to pivot on shaft 72 in response to the rotation of cam lever 240. Cam disk 250 is illustrated in FIG. 6 as having two detents 254 on its outer face that interact with two bumps (not shown) on the side of slot 73 to preferably hold it in either of the two positions shown in FIGS. 5 and 6. The ball 244 sits in the bore 256 of lever 22 and allows lever 22 to change angle in response to rotation of the cam lever 240 and the relative positions of the angled faces of disks 242 and 250.

Figure 12:
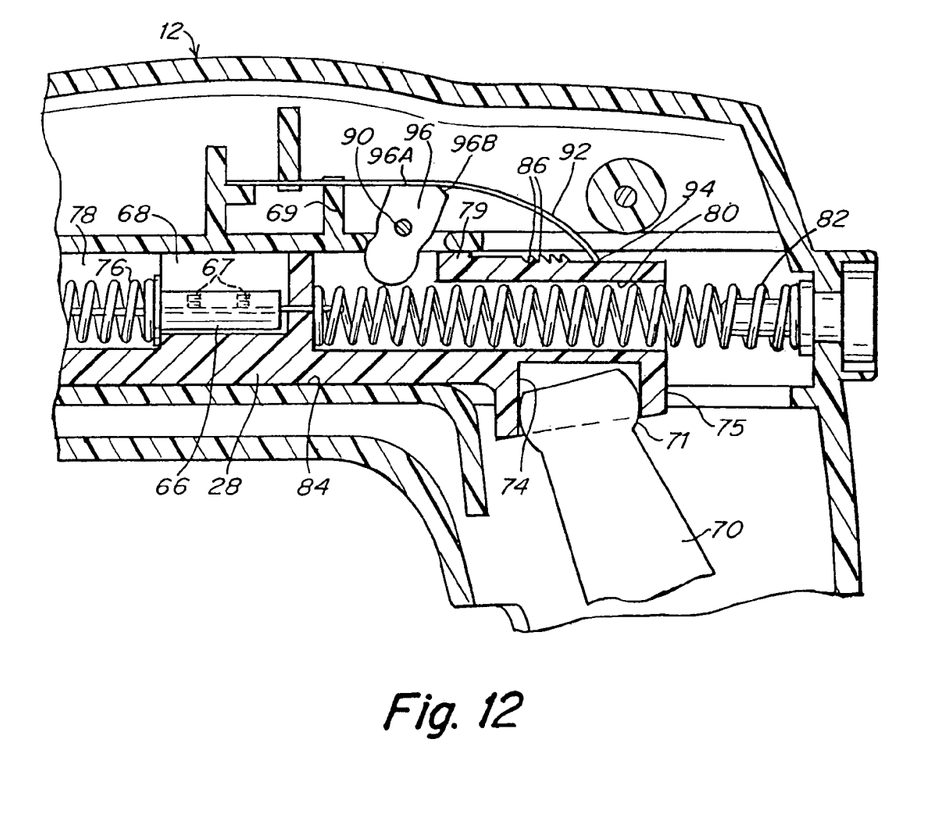
FIGS. 12-14 are somewhat schematic enlarged fragmentary cross-sectional views of the handle basically taken along line 12-12 of FIG. 7 showing the operation of the jaw clamping lever means for different positions thereof.
Figure 13:
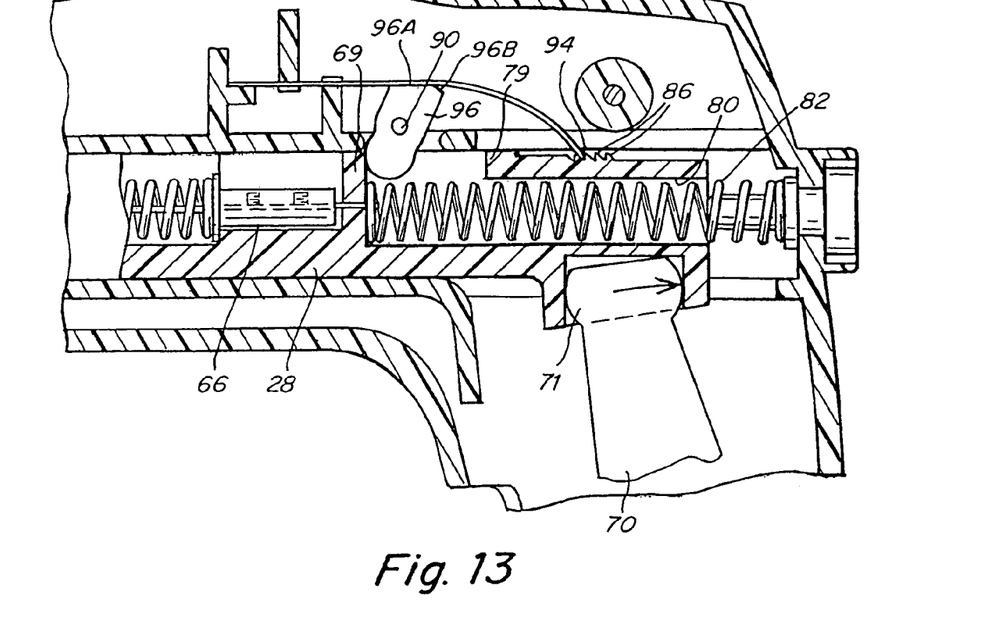
Figure 14:
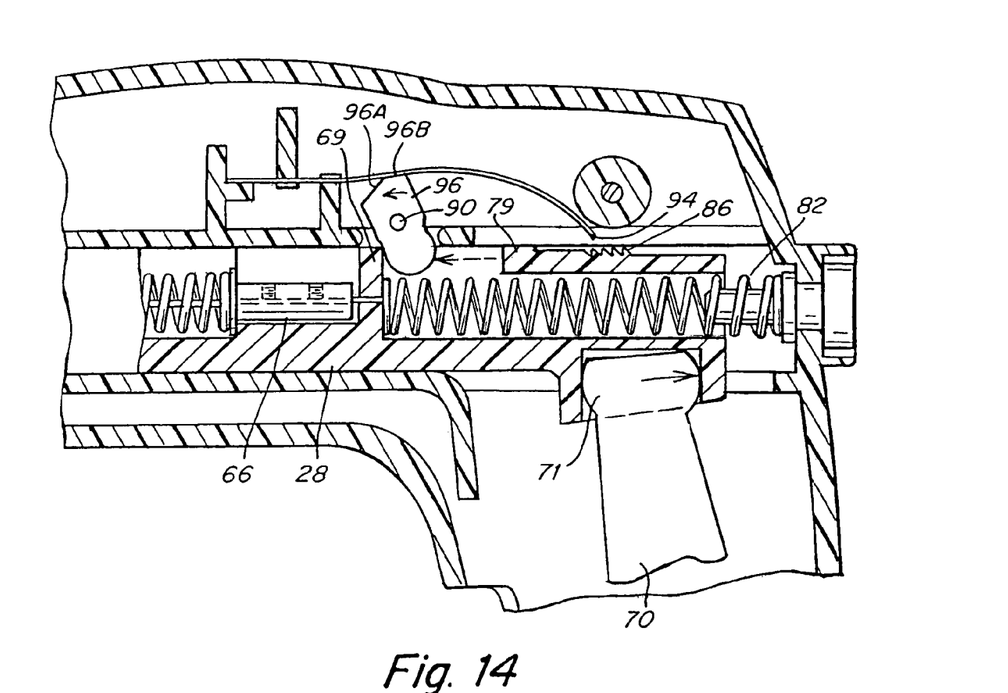

The jaw clamping means 30 uses a ratcheting and release mechanisms and is shown in a series of positions in FIGS. 12-14. The ratcheting mechanism is illustrated by the leaf spring 92 with an angled end 94 that engages teeth 86 on the slider 28 as lever 22 is squeezed. FIG. 12 shows the mechanism in an initial position, such as the position shown in FIG. 2 corresponding to an open position of the jaws. FIG. 13 shows the clamping lever at an advanced position with the end 94 of the spring 92 engaging one of the teeth 86 on the slider 28. For release of the jaws, the lever 22 is squeezed all the way to the position of FIG. 14 at which point, wall 69 contacts latch 96 and rotates latch 96 counterclockwise around pivot 90 until spring 92 is lifted out of engagement with the teeth 86 by the latch face 96B engaging the underside of the spring 92. FIG. 14 shows the leaf spring 92 being lifted so as to disengage from the ratchet teeth 86. This action leaves the slider 28 free to move to the left as seen in FIG. 14 until wall 79 contacts and rotates the latch 96 clockwise around pivot 90 until face 96A is aligned with the underside of the spring, allowing it to drop into place for engagement with the end of the slider 28 just to the rear of the teeth 86, as in the position illustrated in FIG. 12.

The spring 92 and the teeth 86 form a ratchet arrangement in which the lever 22 may be clicked through a number of positions in closing the end effector and tightening the jaws of the end effector about an item such as a needle. As the lever 22 is depressed inwardly toward the handle, then the free end 94 of the latch spring 92 engages with various teeth on the slider. The jaws are tightened by each successive click until the item being grasped is fully engaged. In order to release the actuation sequence, rather than using a separate release button, the lever 22 is simply moved to its most inward position such as illustrated in FIG. 14 where the latch 96 engages the wall 79. This pivots the latch to a position where it lifts the spring 92 thus disengaging the spring from the teeth on the slider and enabling the slider to thus move under spring bias to its released position.

The locking mechanism or angle locking means 140 of the present invention includes a ball and socket arrangement that is basically disposed over the proximal bendable member and that follows the bending at the proximal bendable member. The locking mechanism has locked and unlocked positions, is disposed about the proximal movable or bendable member and is manually controlled so as to fix the position of the proximal movable member relative to the handle in the locked position thereof. The locking mechanism comprises a ball member and a compressible hub that defines a socket member. In the disclosed embodiment the hub is a split hub and the locking mechanism further includes a cinch ring disposed about the split hub and a locking lever mounted on the cinch ring for closing the cinch ring about the hub to lock the hub against the spherical ball member. The cinch ring interlocks with the hub but is able to rotate relative thereto when in the unlocked position.

The "ball" part is basically formed by the ball member 120, while the "socket" part is basically formed by an extension of the handle, namely the split hub 202. The locking mechanism locks the proximal bendable member in a desired position and by doing that also locks the position of the distal bendable member and tool. The proximal bending member 18, although it is enclosed the ball and socket arrangement, still allows the instrument shaft 14 and the proximal bending member 18, along with the cabling 100, to rotate freely while also allowing the axis of the instrument shaft to be angled relative to the axis of the handle in a free, or alternately, locked mode.

For this purpose refer to the ball member 120 which is shown in further detail in FIGS. 5-8. The ball member 120 includes a distal neck 206 that is contiguous with a partially spherical ball end having a spherical outer surface 204. The neck 206 is basically disposed over the adaptor 26 and conical portion 19 of the proximal bendable member 18, while the ball portion is mainly disposed over the primary part of the proximal bendable member 18. The ball member 120 is adapted to sit within a socket that is formed in the handle in the form of a hub 202 that can be collapsed about the ball member 120 by radially compressing the cinch ring 200.

The ball member 120 is gimbaled in a split hub 202 that is comprised of four quadrants 202A-202D that can be clamped against the spherical surface 204 of the ball member 120 by means of the cinch ring 200. Refer to FIG. 8. The split hub 202 is supported at the distal end of the handle by means of three struts 230 that are spaced approximately 120 degrees apart (see FIG. 11). The ball member 120 has a neck portion 206 that provides support for the distal end of the proximal bendable member 18. In this regard a bearing surface 208 is provided, as illustrated in FIGS. 7 and 8, between the proximal end of the neck 206 and the adaptor 26. This enables the proximal bendable member, along with the adaptor 26 to be free to rotate relative to the ball member 120. FIGS. 7 and 8 also illustrate a bearing surface at 210 between the very distal end of the neck 206 and the outer tube 32. These bearing surfaces 208, 210 may be formed by actual bearings at those locations.

FIGS. 5-8 illustrate the cinch ring 200. Refer also to FIGS. 2 and 3 for an illustration of the cinch ring 200. The cinch ring 200 is an annular member that has an internal ridge or spline 201 that is adapted to mate with a channel or groove 203 in the outer surface of the split hub 202. This combination of a channel and ridge limits the annular cinch member to just rotation about the hub 202. FIG. 8 also shows that each of the portions 200A-200B of the split hub connects to the instrument handle via respective struts 230 (see also FIG. 11). When the cinch ring 200 is closed this, in turn, closes the slotted hub and essentially compresses the socket (hub 202) against the spherical surface 204 of the ball member 120. The locking of the ball member thus fixes the position of the proximal bendable member, and, in turn, the distal bendable member and tool.

The cinch ring 200 is operated by means of an over-center locking lever 220 that is connected to ends 200A and 200B of the cinch ring 200 by means of the pins 222 and 224, respectively. FIG. 5 illustrates the lock lever 220 in a locked position while FIG. 6 illustrates the lock lever in a released or unlocked position. The end 200A of the cinch ring 200 is in the form of a detachable hook that snap fits over pin 222 and sits in a slot 226 of the lever 220 when the ring is locked. The other end 200B of the cinch ring 200 is in the form of two bales that snap fit over pin 224 formed on the sides of the lever 220. The cinch ring 200 is free to rotate around the split hub 202 when lever 220 is released by means of the spline 201 that rides in the groove 203 in the circumference of the split hub 202. This allows for left or right handed operation of the instrument. FIG. 5 illustrates a set up for a right handed operation with the angle locking lever 220 shown in a locked position and FIG. 6 illustrates a set up for a left handed operation, with the angle locking lever 220 shown in an unlocked position.

When the locking lever 220 is moved to its locked position this compresses the cinch ring 200 closing the hub against the spherical outer surface 204 of the ball member 120. This locks the handle against the ball member 120 holding the ball member in whatever position it is in when the locking occurs. By holding the ball member in a fixed position this, likewise, holds the proximal bendable member in a particular position and fixed in that position. This, in turn, maintains the distal bendable member and tool at a fixed position, but the instrument orientation can be controlled via the control of the rotation knob which controls the orientation of the instrument tip by enabling rotation of the distal bendable member and tool about the tip axis P (see FIG. 3).

The instrument of the present invention provides an improved instrument, particularly from the standpoint of ease of use by the surgeon. The tool actuation lever arrangement permits fine control by the user, particularly with the instrument arrangement that has the recessed gimbal where the finger of the user can be readily engaged with the lever. This arrangement also enables the instrument to be readily adapted for either right-handed or left-handed control by simply rotating the gimbal in its socket between opposite positions. It is also preferred that the recess in the gimbal be formed by a blind hole (with a bottom wall) as this has been found to provide enhanced manual control of the lever positioning.

Another improvement of the instrument of the present invention relates to the ease with which the tool can be controlled including the convenient placement of the rotation member and the convenient placement of the locking arrangement where the users thumb and forefinger can be readily used to control both tip rotation as well as locking. These functions can be performed with a single hand and without requiring the user to move the hand position.

Having now described a limited number of embodiments of the present invention it should now be apparent to one skilled in the art that numerous other embodiments and modifications are contemplated as falling within the scope of the present invention as defined by the appended claims. For example, in another version of the present invention a different form of instrument tip rotation means may be used such as a slide mechanism to control distal rotation about the tool tip axis. Even with such alternate means a locking function may still be associated with the instrument to provide the lock function. The locking means described herein has been illustrated for use with a pistol grip handle, however, this locking means may also be provided on an in-line instrument such as the type illustrated in Ser. No. 11/185,911 filed on Jul. 20, 2005. Also, in the instrument that is described herein the movable members have been illustrated as bendable sections, and more particularly, as unitary bendable sections. However, the movable members may alternatively be of other constructions including, but not limited to, engageable discs, bellows arrangements, a movable ring assembly or ball and socket members. For other forms of bendable members refer to co-pending provisional application Ser. No. 60/802,885 filed on May 23, 2006 and 60/811,046 filed on Jun. 5, 2006, both of which are hereby incorporated by reference herein in their entirety. Also, in the instrument that is described herein the ball and socket arrangement has the ball part on a separate member that mates with a socket associated with the handle. In still another embodiment of the present invention the ball and socket arrangement may comprise a separate socket member that mates with a protruding ball of the handle.

What is claimed is:

1. A surgical instrument comprising:
an instrument shaft having proximal and distal ends and a longitudinal axis;
a tool disposed from the distal end of the instrument shaft;
a control handle coupled from the proximal end of the instrument shaft and including proximal and distal sides and an axis extending therebetween;
a distal motion member for coupling the distal end of said instrument shaft to said tool;
a proximal motion member;
actuation means extending between said distal and proximal motion members for coupling motion of said proximal motion member to said distal motion member for controlling the positioning of said tool;
an angle locking mechanism for fixing the position of the tool at a selected position and having locked and unlocked states;
said angle locking mechanism including a ball and socket arrangement disposed between the control handle and the instrument shaft and manually operable to selectively control a fixing of a bend angle between the respective axes of the instrument shaft and control handle;
said ball and socket arrangement including a socket member having an inner partially spherical shaped surface, and a ball member having an outer partially spherical shaped surface that mates with the partially spherical shaped socket surface so as to enable motion between the ball member and the socket member;
said ball member supported within said socket member and constructed and arranged to enable manual control of the bend angle between the respective axes of the instrument shaft and control handle;
said angle locking mechanism further including a manually operable locking lever mounted at the control handle and that, when moved to the locked state, provides a radial compression between the socket member and the ball member so as to fix the relative position between the socket member and the ball member to, in turn, fix the position of the distal motion member and tool;

a rotation knob mounted at the control handle and rotatable relative to the control handle for causing a corresponding rotation of the tool; and a tool actuation mechanism mounted at the proximal side of the control handle, said rotation knob adapted to rotate the tool about a distal tool roll axis and said rotation knob is disposed between said tool actuation mechanism and said locking lever.

2. The surgical instrument of claim 1 wherein the rotation knob controls tool rotation in both the locked and unlocked states of the angle locking mechanism.

3. The surgical instrument of claim 2 wherein said actuation means includes actuation cabling.

4. The surgical instrument of claim 1 wherein said control handle comprises a pistol grip handle having an engagement horn to assist in holding the handle.

5. The surgical instrument of claim 2 wherein said rotation knob is disposed closer to the distal side of the control handle than the proximal side of the control handle.

6. The surgical instrument of claim 1 wherein said tool actuation mechanism includes a tool actuation lever, and said control handle includes a pistol grip handle with the tool actuation lever supported from said pistol grip handle at a pivot point toward the proximal side of the pistol grip handle.

7. The surgical instrument of claim 6 wherein said actuation lever has a free end with a finger loop for receiving a users finger to control the lever.

8. The surgical instrument of claim 1 wherein said tool actuation mechanism includes a tool actuation lever, a tool actuation cable that extends from said tool to said tool actuation lever, a slider for capturing a proximal end of said tool actuation cable, said tool actuation lever supported at said handle for controlling the translation of said slider and, in turn, said tool actuation cable.

9. The surgical instrument of claim 8 including a slideway for receiving said slider, a pair of springs disposed in said slider and a rotational barrel disposed between said springs and for holding the proximal end of said tool actuation cable.

10. The surgical instrument of claim 1 wherein the socket member is formed by a hub that is integrally attached at the distal side of the control handle.

11. The surgical instrument of claim 1 wherein said control handle has a distal collar with the socket formed on the inner surface of the collar and an annular cinch ring that is disposed about said distal collar.

12. The surgical instrument of claim 11 including a tongue and groove interconnection between said cinch ring and collar so as to permit rotation therebetween while preventing axial movement.

13. The surgical instrument of claim 12 including a pivot piece on said cinch ring having opposed locked and unlocked positions.

14. The surgical instrument of claim 11 wherein said distal collar has one or more slots to enable the socket to be compressed about the ball member as the cinch ring is locked.

15. The surgical instrument of claim 1 wherein at least a part of said proximal motion member is captured inside a hollow chamber defined in the ball and socket arrangement.

16. The surgical instrument of claim 1 wherein the ball member of the ball and socket arrangement comprises a hollow ball member having an internal hollow chamber with at least a portion of the proximal motion member supported within the hollow chamber.

17. The surgical instrument of claim 1 wherein the socket member is integrally formed with the control handle at the distal side of the control handle.

18. The surgical instrument of claim 2 wherein the locking lever is mounted at the control handle at a position distally of the rotation knob.

19. A surgical instrument comprising:

an instrument shaft having proximal and distal ends and a longitudinal axis;

a tool disposed from the distal end of the instrument shaft;

a control handle coupled from the proximal end of the instrument shaft and including proximal and distal sides and an axis extending therebetween;

a distal motion member for coupling the distal end of said instrument shaft to said tool;

a proximal motion member;

actuation means extending between said distal and proximal motion members for coupling motion of said proximal motion member to said distal motion member for controlling the positioning of said tool;

an angle locking mechanism for fixing the position of the tool at a selected position and having locked and unlocked states;

said angle locking mechanism including a ball and socket arrangement disposed between the control handle and the instrument shaft and manually operable to selectively control a fixing of a bend angle between the respective axes of the instrument shaft and control handle;

said ball and socket arrangement including a socket member having. an inner partially spherical shaped surface. and a ball member having an outer partially spherical shaped surface that mates with the partially spherical shaped socket surface so as to enable motion between the ball member and the socket member;

said ball member supported within said socket member and constructed and arranged to enable manual control of the bend angle between the respective axes of the instrument shaft and control handle;

said angle locking mechanism further including a manually operable locking lever mounted at the control handle and that, when moved to the locked state, provides a radial compression between the socket member and the ball member so as to fix the relative position between the socket member and the ball member to, in turn, fix the position of the tool;

a rotation knob mounted at the control handle and rotatable relative to the. control handle for causing a corresponding rotation of the tool about a distal tool roll axis;

said locking lever being mounted at the control handle at a position distally of the rotation knob; and wherein the locking lever has a maximum radially extending dimension, measured from the control handle axis, that is greater than the maximum radius of the rotation knob.

20. The surgical instrument of claim 19 wherein the locking lever has a maximum radially extending dimension, measured from the control handle axis, that is greater than the maximum radius of the rotation knob in both the locked and unlocked states of the angle locking mechanism.

21. The surgical instrument of claim 20 wherein the rotation knob is disposed adjacent to the locking lever in the direction of the control handle axis.

22. The surgical instrument of claim 19 including a tool actuation mechanism disposed at the proximal side of the control handle.

23. The surgical instrument of claim 22 wherein the rotation knob is disposed adjacent to the locking lever in the direction of the control handle axis.

24. The surgical instrument of claim 23 wherein said rotation knob is disposed between said tool actuation mechanism and said locking lever.

25. The surgical instrument of claim 19 wherein said actuation means includes actuation cabling.

26. The surgical instrument of claim 19 wherein the tool is controllable via the rotation knob for rotation in both the locked and unlocked state of the locking lever.

* * * * *